United States Patent [19]

Ichijima et al.

[11] 4,118,732
[45] Oct. 3, 1978

[54] APPARATUS FOR DETECTING A SURFACE FLAW OF A MATERIAL AT HIGH TEMPERATURE

[75] Inventors: Isamu Ichijima, Kisarazu; Seiichi Watanabe, Kimitsu; Kazuo Miyagawa, Kisarazu, all of Japan

[73] Assignee: Nippon Steel Corporation, Tokyo, Japan

[21] Appl. No.: 768,822

[22] Filed: Feb. 15, 1977

[51] Int. Cl.² .................................................. H04N 7/18
[52] U.S. Cl. ........................... 358/101; 250/333; 358/106; 358/113; 358/163
[58] Field of Search ............... 358/101, 106, 110, 113, 358/100, 163; 250/330, 333, 334

[56] References Cited
U.S. PATENT DOCUMENTS

| | | | |
|---|---|---|---|
| 3,158,748 | 11/1964 | Laycak | 358/106 |
| 3,256,435 | 6/1966 | Astheimer | 358/113 |
| 3,748,383 | 7/1973 | Grossman | 358/113 |
| 3,812,483 | 5/1974 | Graves | 358/113 |
| 3,909,521 | 9/1975 | Hunt | 358/113 |
| 3,946,232 | 3/1976 | Harmer | 250/333 |
| 3,988,530 | 10/1976 | Ikegami | 358/106 |

*Primary Examiner*—Howard W. Britton
*Attorney, Agent, or Firm*—Wenderoth, Lind & Ponack

[57] ABSTRACT

The present invention is an apparatus for detecting a surface flaw in hot metal including a particularly designed television camera, a shutter means and a control circuit which compensates the television camera's shading as well as the temperature difference among normal parts of the observed material.

The apparatus makes it possible to conduct clear detection of a flaw on the surface of the hot material as it is so that yield loss at the time of scarfing can be avoided while heat energy can effectively be utilized.

5 Claims, 28 Drawing Figures

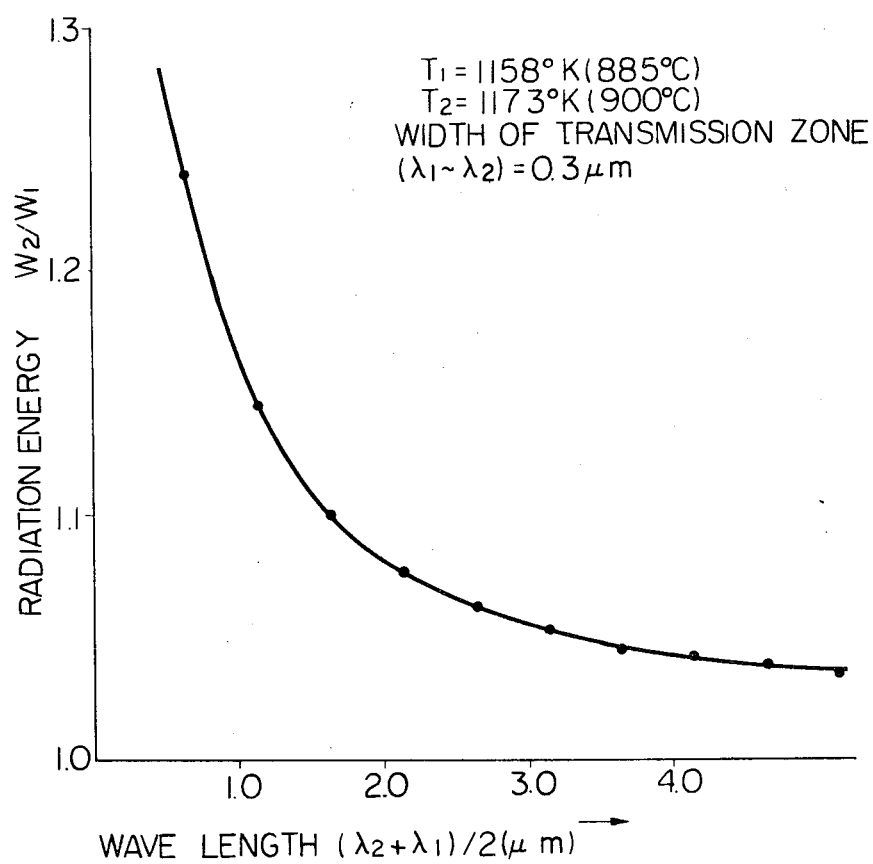

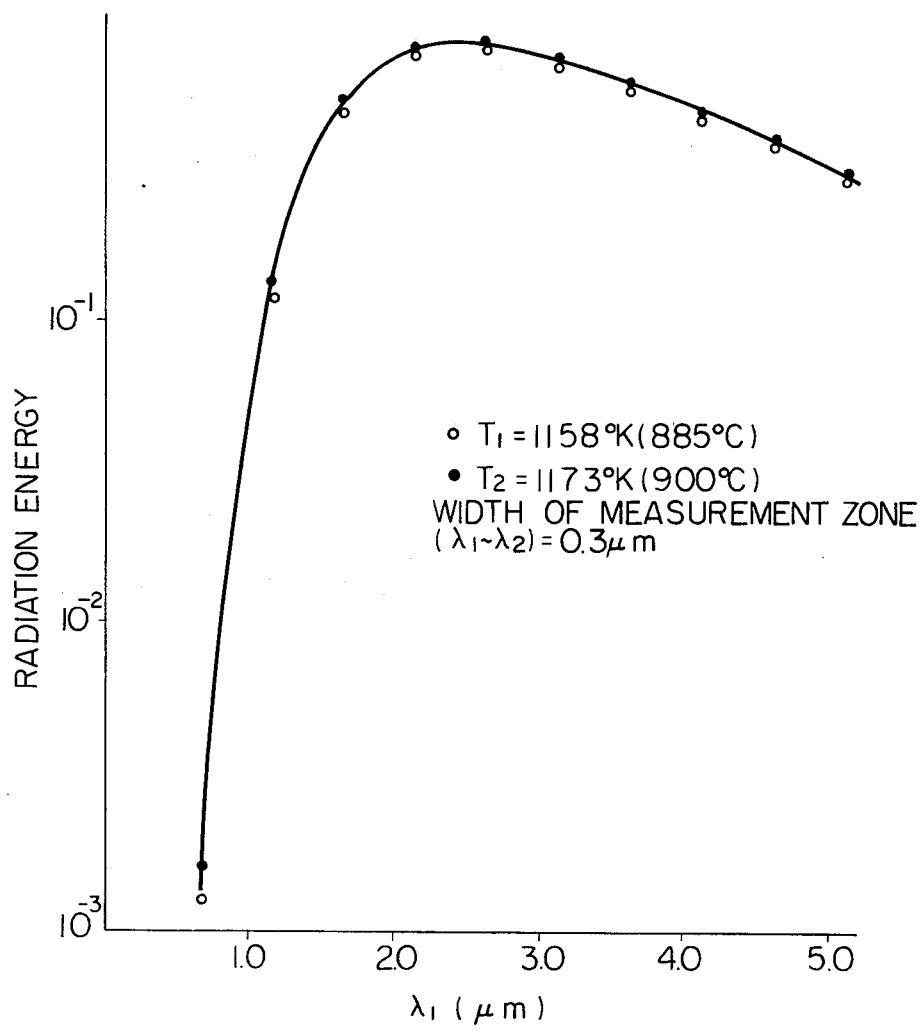

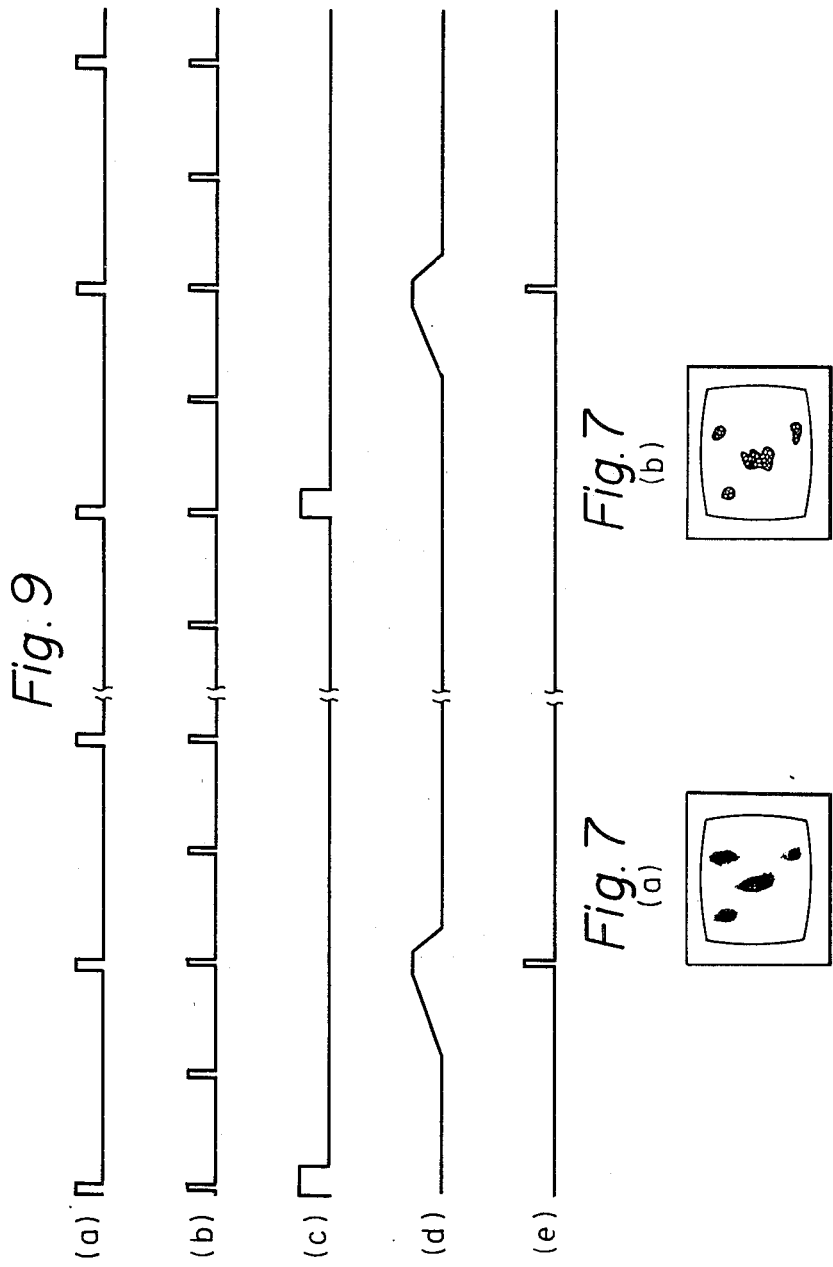

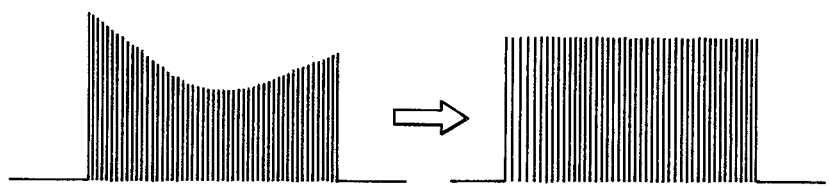
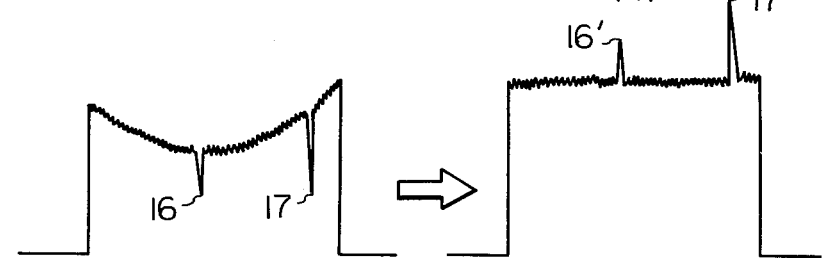
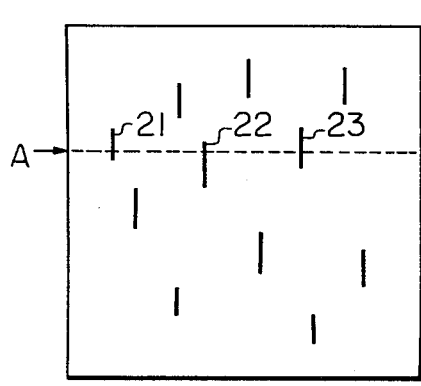
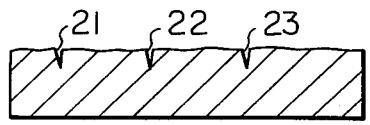

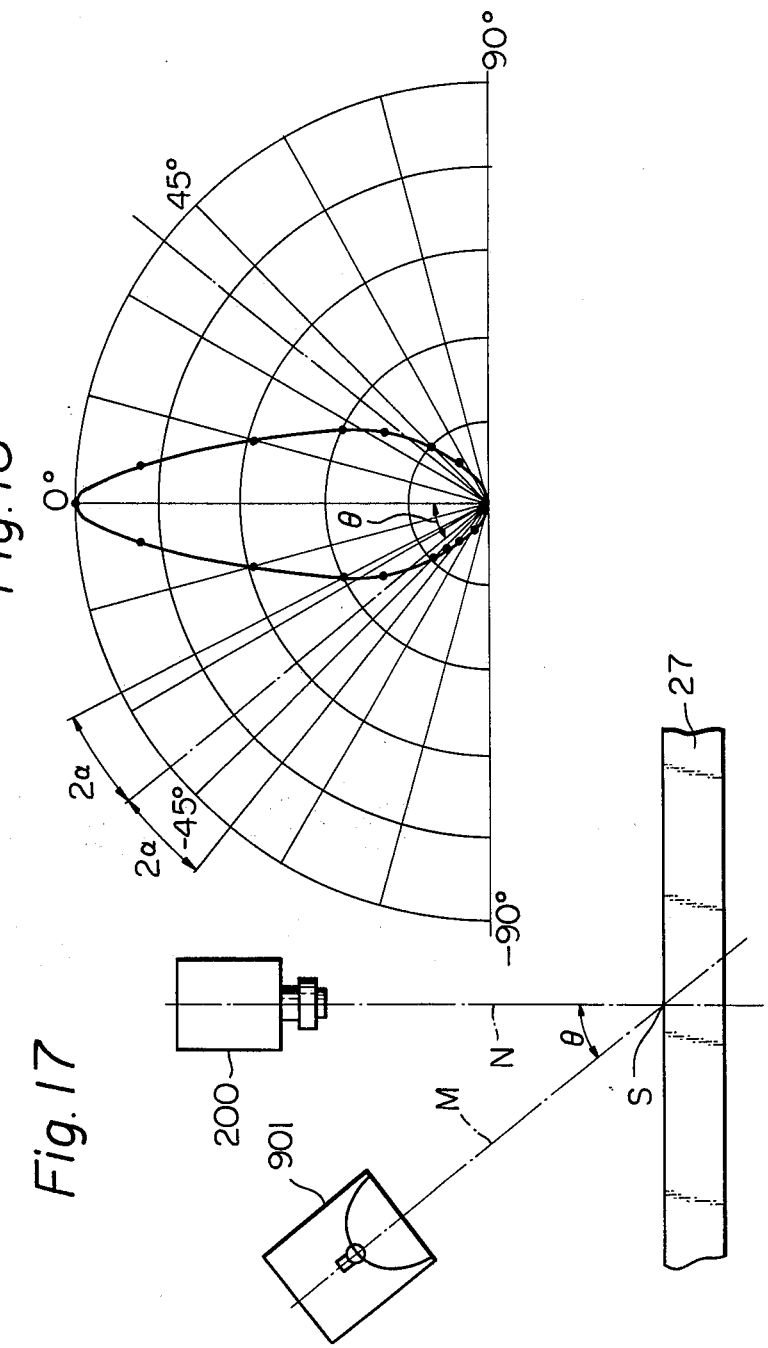

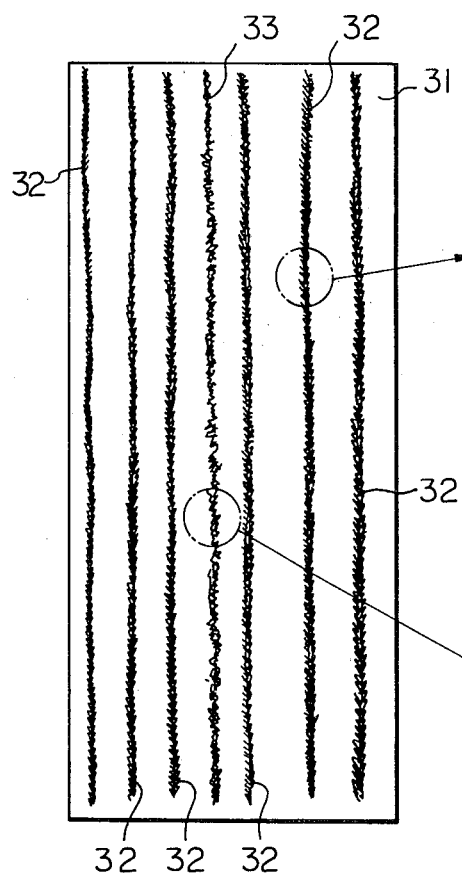
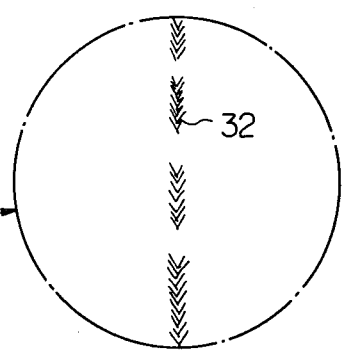
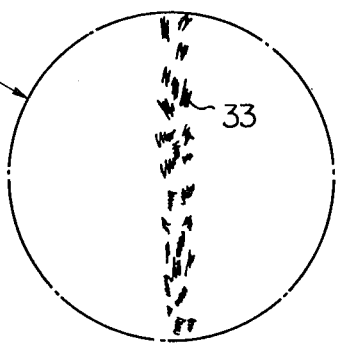
Fig. 19 (a)
Fig. 19 (b)
Fig. 19 (c)

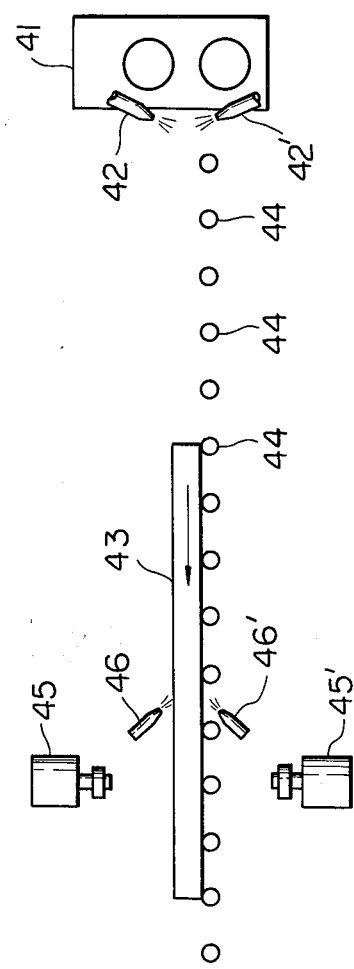

APPARATUS FOR DETECTING A SURFACE FLAW OF A MATERIAL AT HIGH TEMPERATURE

DETAILED DESCRIPTION OF THE INVENTION

This invention relates to a method for detecting a surface flaw in a material, especially a hot metal such as steel, by photoelectrically measuring the radiation energy emitting from the material in the high temperature range and/or the reflected energy of a light ray irradiating the surface of the material and calcualting the difference in the measured energy based on the temperature difference beteween a normal part and a defective part of the material.

As one of the above stated methods for detecting a surface flaw, it has heretofore been proposed to detect the surface flaw by detecting the infrared rays radiated by the hot metal, using an infrared photoelectric conversion element. Fundamentally speaking, the above stated object can be accomplished even by this infrared detecting method.

However, there is in fact some fluctuation in the surface temperature of the hot metal even in its normal parts, and there is also some fluctuation in the scale of the surface thereof. for these and other reasons, it is impossible to fully detect the difference of radiation energy between a normal part and a defective part in view of the fluctuation of radiation energy of the normal part. As a result, this method for detecting a surface flaw by detecting the infrared rays has not yet been feasible.

Based upon detailed experiments and theoretical analysis about the above stated method for detecting a surface flaw by the difference of radiation energy, a television camera is used in the practice of this invention as a means to detect the optimum radiation energy and the optimum reflection energy of an irradiated ray for detecting a surface flaw of the hot metal.

According to this invention there is provided an apparatus for detecting a surface flaw of a material to be measured wherein the radiation energy emitting from the surface of this material in high temperature range and/or the reflected energy of a strobo light flash irradiating the surface of the material is detected by means of a photoelectric detector so as to detect a surface flaw of this material, which comprises, (1) a television camera for detecting the radiation energy and/or the reflected energy from the surface of the material, (2) a shutter means provided before an image pick up tube of the television camera to obtain the rest image of the moving material by the television camera, (3) a shading control circuit providing between the output terminal of the television camera and the input terminal of a circuit for recognizing defects for corresponding the output fluctuations within the image pick up plane of the image pick up tube of the television camera.

A theoretical and experimental explanation demonstrating the fact that the television camera is suitable as a means for detecting the radiation energy emitting from the surface of a hot metal is described below with reference to the drawings.

FIG. 2 is a graph showing the relation of the wave length $\lambda$ and the ratio $W_2/W_1$ when the width of the transmission wave length zone ($\lambda_1 \sim \lambda_2$) is made constant.

FIG. 3 is a graph showing the relation of the wave length $\lambda_1$, and the radiation energy.

FIGS. 4 and 5 show a signal wave patern obtained by scanning a predetermined range of the surface of the material when the visual field of the photoelectric conversion element is made spot-like.

FIG. 7 (a) and (b) are the flowing or broken rest image and the normal rest image, respectively.

Figure 8:
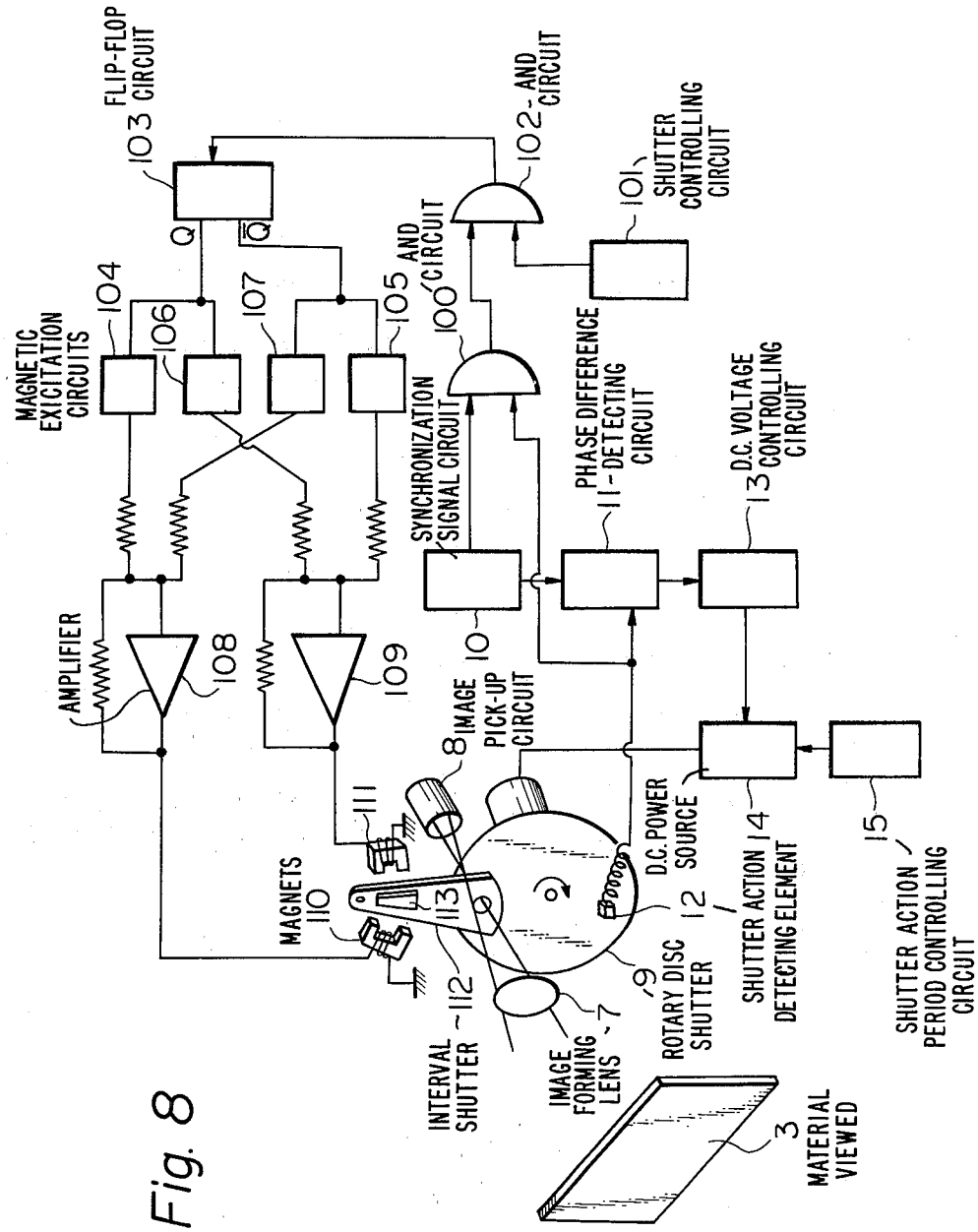

FIG. 8 is an electric block diagram of one example of the shutter means used in this invention.

FIG. 9 illustrates the timing patterns of actions of the high speed shutter means shown in FIG. 8.

FIG. 10 (a) and (b) are signal wave patterns before the shading correction and after the shading correction, respectively.

FIG. 11 (a) and (b) are similar to FIG. 10 (a) and (b), except that they concern one horizontal scanning line taken from those of FIG. 10 (a) and (b), respectively.

Figure 12:
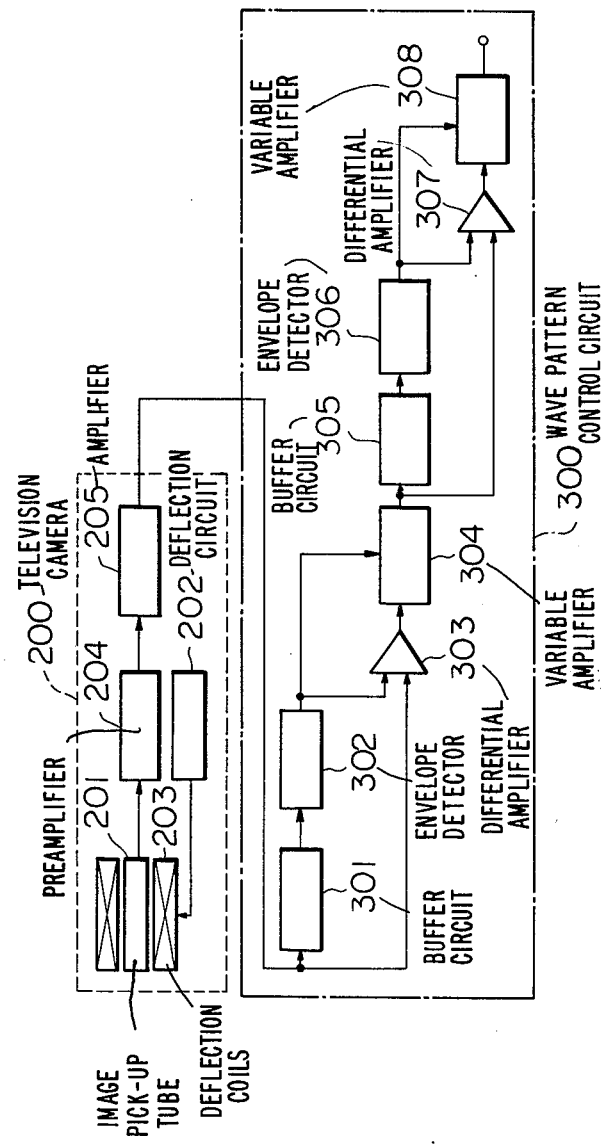

FIG. 12 is a block diagram showing one example of the shading correction circuit used in this invention.

FIG. 13, 14, 15a and 15b show typical examples of the surface flaws appearing on the surface of the material.

Figure 16:
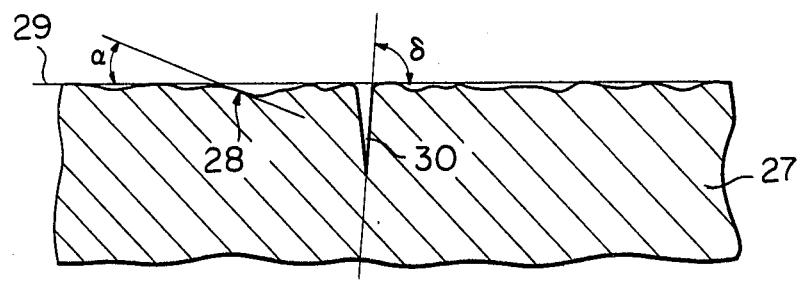

FIG. 16 is a schematic view of the material surface condition of the including normal part and a defective part.

FIG. 17 is a schematic view showing the irradiation angle of an strobe light.

FIG. 18 is a graph showing the reflection behavior of the light.

FIGS. 19a, 19b and 19c are schematic views illustrating the surface condition of a material subjected to hot scarfing.

FIG. 20 is a view explaining a method for detecting a surface flaw of a hot steel material after slabbing.

The spectral intensity of the radiation energy radiated from a substance is generally represented by the following formula:

$$Me\lambda = \frac{\epsilon C_1}{\lambda^5} (e^{C_2/\lambda T} - 1)^{-1} \quad (1)$$

Figure 1:
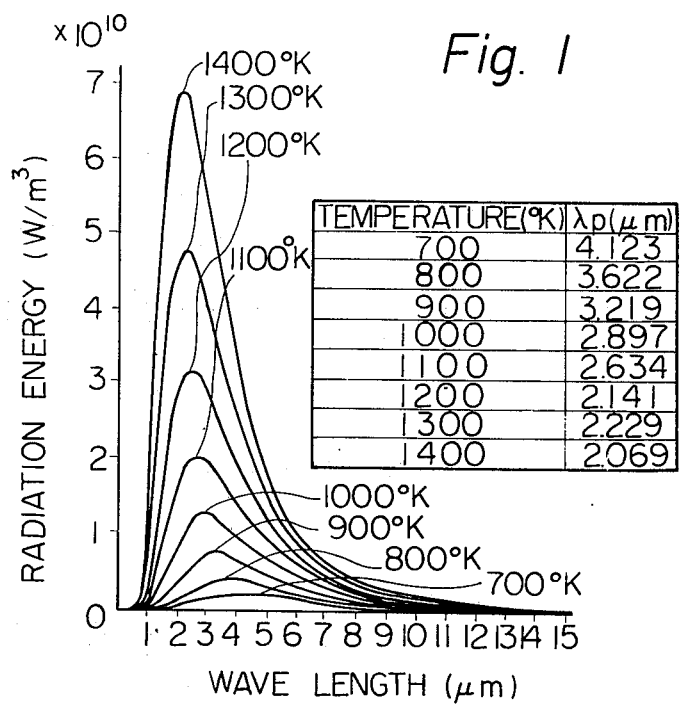
FIG. 1 is a diagram showing the relation of the wave length and the radiation energy of a black body.

$Me\lambda$: radiation energy(Watt/cm$^3$)
$C_1$: $3.7402 \times 10^{-12}$ Watt. cm$^2$
$C_2$: 1.43848 cm. °K
T: Absolute Temperature (°K) of the radiator
$\lambda$: Wave length (cm) of the radiation
$\epsilon$: Emissivity of the radiator In the diagram of FIG. 1 the wave length $\lambda p$, which represents the maximum spectral intensity of the radiation energy, yields the values as indicated. It is to be noted in FIG. 1 that the difference between the radiation energy from a black body at a temperature of $T_1$ and that from a black body at a temperature of $T_2$ is larger in the shorter wave lengths than in the longer wave lengths, the wave length $\lambda_p$ representing the maximum spectral intensity being the boundary. This means that the difference of radiation energy caused by the difference of temperature of the surface of a material, e.g., a hot steel material is also larger in the shorter wave lengths than the wave length $\lambda p$.

This is further explained in detail below.

In case an optical band pass filter which has a transmission coefficient of zero for the wave lengths shorter than $\lambda_1$, that of 1.0 for wave lengths between $\lambda_1$ and $\lambda_2$ and that of zero for wave lengths exceeding $\lambda_2$ is positioned before a radiation energy detector and the radiation energy $W_1$ from a surface at a temperature $T_1$ and the radiation energy $W_2$ from a surface at a temperature $T_2$ are respectively measured, the ratio $W_2W_1$ is represented by the following formula:

$$\frac{W_2}{W_1} = \frac{\int_{\lambda_1}^{\lambda_2} Me\lambda d\lambda(T_2)}{\int_{\lambda_1}^{\lambda_2} Me\lambda d\lambda(T_1)} \quad (2)$$

As is obvious from FIG. 2, the difference or the ratio of radiation energy, that is, $W_2/W_1$ becomes larger as the wave length $\lambda_1$ or $\lambda_2$ becomes smaller.

From the above, it can be seen that, when it is desired to detect any surface flaw of a material by detecting the difference of radiation energy based on the difference of temperature between a normal part and a defective part of the material, the difference of radiation energy between the normal part and the defective part becomes larger if the radiation energy is measured on the side of shorter wave lengths, particularly on the side of wave lengths shorter than the wave length which gives the maximum radiation energy.

In this invention, the temperature of a hot metal, the surface flaw of which is to be detected, may range from about 650° C to about 1200° C. In this temperature range, the wave length $\lambda p$ which gives the maximum radiation energy is about 2 $\mu$m to 3 $\mu$m. In this case, however, the radiation energy over the entire range of wave lengths is itself small and, particularly, the radiation energy on the side of wave lengths shorter than $\lambda p$ is small. Therefore, the radiation energy which is to be measured becomes extremely small as is clear from the experimental example shown in FIG. 3.

If the radiation energy to be measured is small, the accuracy of detection of the difference of the radiation energy between the normal part and the defective part becomes lowered in view of noise. Accordingly, the band of measurement can not be set substantially on the side of shorter wave lengths. That is, in the case of a measurement system constituted by amplifying a photoelectric conversion signal, there exists shot noise in the photoelectric conversion element and the photo cathode themselves, shot noise in the amplifier and a thermal noise, etc., which may be amplified to form a white noise. If a signal having measurement information is equal to or less than the white noise, the signal may be buried therein, which makes measurement impossible.

Consequently, it is necessary that the output level given by the radiation energy of the normal part should have a value two or more times the value of the white noise and that the difference of the output level caused by the difference of the radiation energy between the normal part and the defective part should have a value fully larger than the value of the white noise.

According to this invention, in a hot metal, the flaw of which is to be detected, experimental results shows that the temperature difference between the normal part and the defective part having a flaw such as, for example, a scab is about 15° C, and the defective part has a lower temperature than the normal part.

Moreover, as a result of actual measurement of the temperature difference between the normal part and the defective part in various flaws of similar hot metal, it has now been ascertained that, as far as the flaw which must be detected in a practical sense is concerned, the temperature difference between the normal part and the defective part is more than about 15° C in respect to any flaw.

Figure 4:
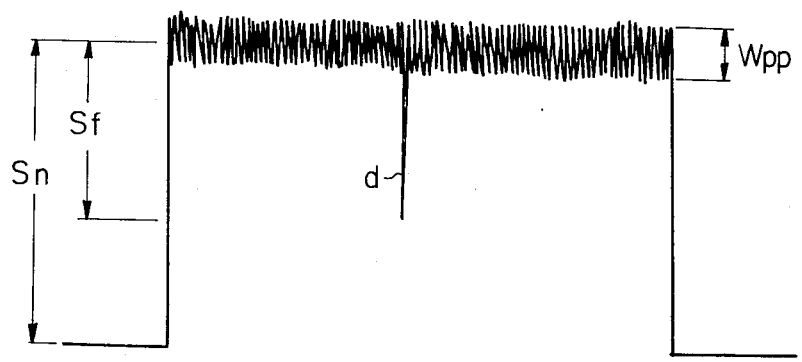
Figure 5:
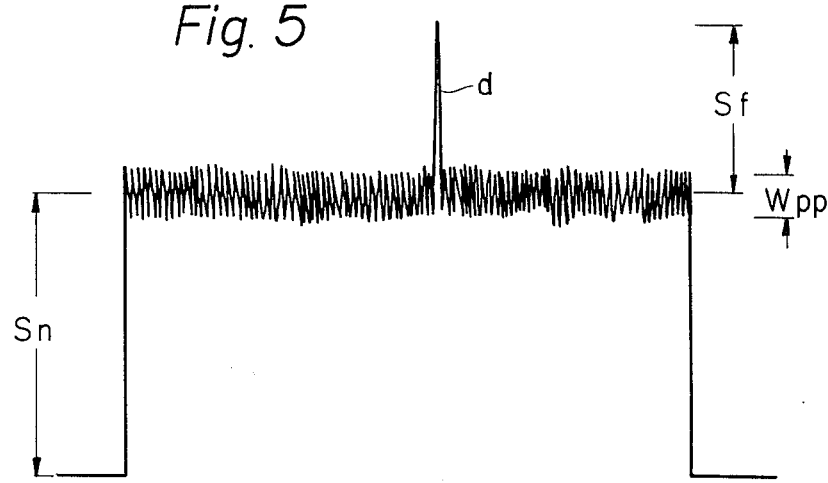

When a predetermined range of the surface of a material is scanned while the visual field of the photoelectric conversion element is made "spot", a signal wave pattern is obtained as shown in FIG. 4. In FIG. 4, Wpp is the peak to peak value of the white noise; Sn is the output level value of the normal part; the $d$ is the flaw signal; and the Sf is the output corresponding to the difference of the radiation energy between the normal part and the defective part.

The results of further tests have clarified that the fluctuation of the output caused by the fluctuation of temperature inside the normal part or by the fluctuation of temperature given by foreign materials such as scales, etc. may exist to the extent of 1.5 times Wpp of the white noise. Then, if this level of 1.5 Wpp is considered as the noize level, it is pre-requisite that the difference of the output level between the normal part and the defective part or Sf should be at least three times Wpp according to the formula below in order to meet the condition under which measurement is practically possible, in which the condition that the ratio of the signal to the noise (S/N) is at least 2. Thus:

$$Sf/Wpp \geq 3 \ldots \quad (3)$$

In carring out the detection of a flaw such as scab in which the temperature of the defective part is lower than that of the normal part as exemplified in FIG. 4, the formula is:

$$Sn \geq Sf \ldots \quad (4)$$

Thus, if it is defined that $Sn/Wpp \equiv a$, the following formula can replace the formulae (3) and (4):

$$Sn/Wpp = a \geq Sf/Wpp \geq 3 \ldots \quad (5)$$

Since the value of the formula (3) has been given as a practically necessary condition, it becomes a problem of what range of the ratio Wh/W1 can meet the formula (3). In this case, Wh is the effective received energy of the radiation energy from the normal or high temperature part, and the WL is the effective received energy of the radiation energy from the defective or low temperature part. Generally, the output Sn of the photoelectric conversion element or the photo cathode has a relation with the irradiated ray W in the dynamic range represented by the formula (6) below:

$$Sn = \alpha W \beta \ldots \quad (6)$$

wherein $\alpha$ and $\beta$ are constants determined by the kind of the photoelectric conversion element or the photo cathode employed.

From the relation of the formula (6) with FIG. 4, the following formulae are given:

$$Sn = \alpha W_h^\beta \ldots \quad (7)$$

wherein $Wh$ is the effective light energy of the radiation energy from the high temperature part or normal part:

$$Sn - Sf = \alpha W^\beta \ldots \quad (8)$$

wherein $Wl$ is the effective light energy of the radiation energy from the low temperature part or defective part.

From the formulae (3) to (8), the following formulae are given:

$$\frac{Sn}{Sn-Sf} = \frac{\frac{Sn}{Wpp}}{\frac{Sn}{Wpp} - \frac{Sf}{Wpp}} = \frac{a}{a - \frac{Sf}{Wpp}} \geq \frac{a}{a-3} \quad (9)$$

$$\frac{Sn}{Sn-Sf} = \frac{\alpha Wh^\beta}{\alpha Wl^\beta} = \left(\frac{Wh}{Wl}\right)^\beta \quad (10)$$

From the formulae (9) and (10), the following is given.

$$\frac{Wh}{Wl} \geq \left(\frac{a}{a-3}\right)^{1/\beta} \quad (11)$$

Accordingly, in the detection of a flaw by which the temperature of the defective part is lower than that of the normal part, the flaw can be detected with the practical accuracy, if a measurement system of radiation energy is constructed in which the ratio of the effective received energy $Wh$ of the radiation energy from the high temperature part (normal part) to the effective received energy $Wl$ of the radiation energy from the low temperature part (defective part), that is $Wh/Wl$, will meet the formula (11).

According to the experimental result in hot metal, the ratio "a" of the output level of the normal part to the peak-to-peak value of the white noise of the measurement system has a value of about 10 to 40. The constant $\beta$ is about 0.67 for a vidicon tube, about 0.87 for a chalnicon tube, about 0.96 for a Si-vidicon tube and about 0.99 under best condition for a phototube or a semiconductor photoelectric conversion element.

Figure 6:
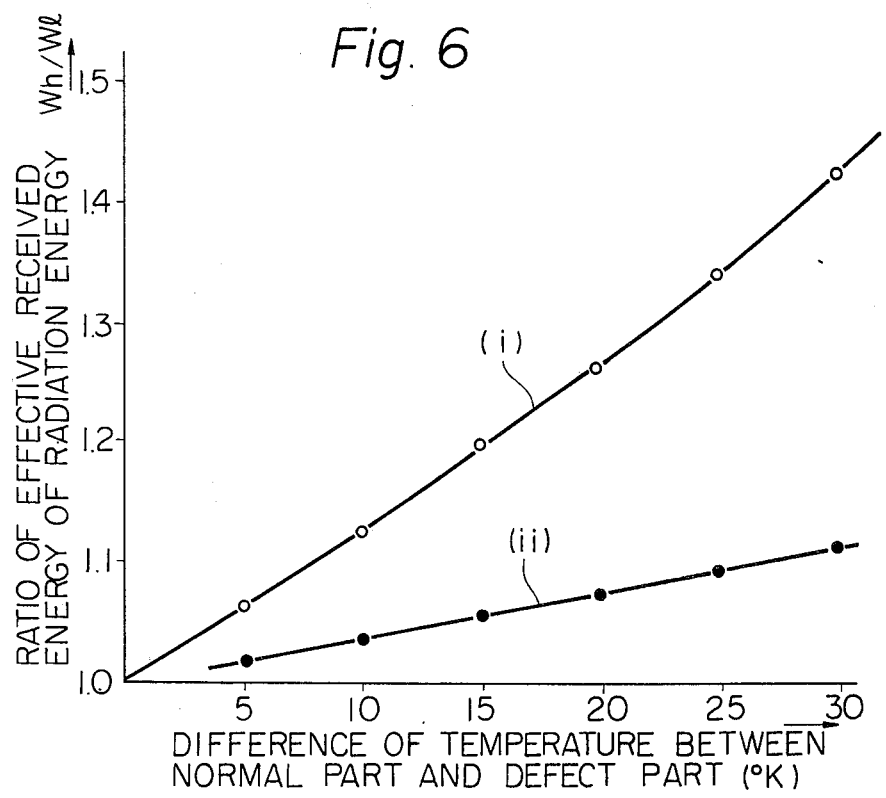
FIG. 6 is a graph showing the relation of (a) the temperature difference between the normal part and the defective part and (b) the ratio Wh/Wl of the efficient received energy of the radiation energy.

In FIG. 6, experimental data are shown about the relation of the temperature difference $\Delta T$ between the normal part and the defective part to the ratio ($Wh/Wl$) of the effective received energy of the radiation energy. This was obtained by the actual measurement with a normal part temperature of 1173° K (900° C) and with of the transmission wave length band being 0.5 μm to 1.0 μm (curve (i)) and 2.0 μm to 5.0 μm (curve (ii)).

From this it is seen that the S/N can be improved to the extent of 3.5 times if the transmission wave length band is set on the side of short wave lengths for the same temperature difference. This can be demonstrated also by the following experiments.

Experiment 1

| | |
|---|---|
| Material to be measured: | Steel slab |
| Temperature of material: | 1150° C (1423 K̊) |
| | $\lambda p = 2.04$ μm |
| Radiation energy detector: | Vidicon tube, Wave length of main sensitive spectra being 0.4 μm to 0.73 μm |

In the case of a scab defect, $$\frac{Wh}{Wl} = \frac{\int_{\lambda_1 = 0.4}^{\lambda_2 = 0.73} Me\lambda d\lambda (Th = 1423 \, K̊)}{\int_{\lambda_1 = 0.4}^{\lambda_2 = 0.73} Me\lambda d\lambda (Tl = 1408 \, K̊)} = 1.179,$$

$$Sn/Wpp = a = 32,$$

and $$\left(\frac{a}{(a-3)}\right)^{\frac{1}{\beta}} = \left(\frac{32}{29}\right)^{\frac{1}{0.67}} = 1.158.$$

It satisfies $$\frac{Wh}{Wl} > \left(\frac{a}{a-3}\right)^{\frac{1}{\beta}}.$$

In the case of detecting a flaw having a higher temperature such as a crack, $$\frac{Wh}{Wl} = \frac{\int_{\lambda_1 = 0.4}^{\lambda_2 = 0.73} Me\lambda d\lambda (Th = 1438 \, K̊)}{\int_{\lambda_1 = 0.4}^{\lambda_2 = 0.73} Me\lambda d\lambda (Tl = 1423 \, K̊)} = 1.179, \text{ and}$$

$$\left(\frac{a+3}{a}\right)^{\frac{1}{\beta}} = \left(\frac{35}{32}\right)^{\frac{1}{0.67}} = 1.1084.$$

It satisfies $$\frac{Wh}{Wl} > \left(\frac{a+3}{a}\right)^{\frac{1}{\beta}}$$

On the other hand, in the case of using, an infrared detector element $Hq(1 - x) Cd(x) Te$ in which the wave length of the main sensitive spectra ranges between 2 μm and 5 μm of the radiation energy detector, the formula:

$$\frac{Wh \, (T_2 = 1423 \, K̊)}{Wl \, (T_1 = 1408 \, K̊)} = 1.042$$

applies to a flaw such as scab having a lower temperature, while the formula:

$$\frac{Wh \, (T_2 = 1438 \, K̊)}{Wl \, (T_1 = 1423 \, K̊)} = 1.042$$

applies to a flaw such as crack having a higher temperature.

With detector element, even if the "a" assumes the maximum $Sn/Wpp = 40$ and the "$\beta$" assumes the maximum value or $\beta = 1$, the following formulae are given:

$$\left(\frac{a}{(a-3)}\right)^{\frac{1}{\beta}} = 40/37 = 1.081, \text{ and}$$

-continued $$\left(\frac{(a+3)}{a}\right)^{\frac{1}{\beta}} = 43/40 = 1.075,$$

then:

$$\frac{Wh}{Wl} < \left(\frac{a}{a-3}\right)^{\frac{1}{\beta}}, \text{ and}$$

$$\frac{Wh}{Wl} < \left(\frac{a+3}{a}\right)^{\frac{1}{\beta}}$$

Accordingly, a satisfactory value for S/N can not be achieved, thus detection with good accuracy can not be effected.

Experiment 2

| | |
|---|---|
| Material to be measured: | Thick steel plate |
| Temperature of material: | 896 ° C (1169 °K) |
| | λp = 2.48 μm |
| Radiation energy detector: | Si-Vidicon tube, Wave length of main sensitive spectra being 0.4μm to 0.73μm |

In case of detecting a flaw such as scab having a lower temperature under the above condition;

$$\frac{Wh}{Wl} = \frac{\int_{\lambda_1 = 0.4}^{\lambda_2 = 0.73} Me\lambda d\lambda (Th = 1169\ °K)}{\int_{\lambda_1 = 0.4}^{\lambda_2 = 0.73} Me\lambda d\lambda (Tl = 1154\ °K)} = 1.195,$$

Sn/Wpp = 35, and $$\left(\frac{a}{a-3}\right)^{\frac{1}{\beta}} = \left(\frac{35}{32}\right)^{\frac{1}{0.96}} = 1.0978$$

It thus satisfies the formula:

$$\frac{Wh}{Wl} > \left(\frac{a}{a-3}\right)^{\frac{1}{\beta}}$$

In case of detecting a flaw such as crack having a higher temperature, $$\frac{Wh}{Wl} = \frac{\int_{\lambda_1 = 0.4}^{\lambda_2 = 0.73} Me\lambda d\lambda Th = 1184\ K}{\int_{\lambda_1 = 0.4}^{\lambda_2 = 0.73} Me\lambda d\lambda (Tl = 1169\ K)} = 1.196, \text{ and}$$

$$\left(\frac{a+3}{a}\right)^{\frac{1}{\beta}} = \left(\frac{38}{35}\right)^{\frac{1}{0.96}} = 1.08944.$$

It thus satisfies the formula:

$$\frac{Wh}{Wl} > \left(\frac{a+3}{a}\right)^{\frac{1}{\beta}}$$

On the other hand, in the case of using, the same infrared detector element Hg(1 − x) Cd (x) Te as above in which the wave length of the main sensitive spectra is in the range of 2 μm to 5 μm as the radiation energy detector, the formulae:

$$\frac{Wh\ (T_2 = 1169\ °K)}{Wl\ (T_1 = 1154\ °K)} = 1.056 \text{ and}$$

$$\left(\frac{a}{a-3}\right)^{\frac{1}{\beta}} = 1.081$$

would apply to a flaw such as scab having a lower temperature, while the formulae:

$$\frac{Wh\ (T_2 = 1174\ °K)}{Wl\ (T_1 = 1169\ °K)} = 1.056 \text{ and}$$

$$\left(\frac{a+3}{a}\right)^{\frac{1}{\beta}} = 1.075$$

would apply to a flaw such as crack having a higher temperature.

Thus, the formulae:

$$\frac{Wh}{Wl} < \left(\frac{a}{a-3}\right)^{\frac{1}{\beta}} \text{ and}$$

$$\frac{Wh}{Wl} < \left(\frac{a+3}{a}\right)^{\frac{1}{\beta}}$$

are satisfied, whereby a satisfactory S/N can not be obtained.

Experiment 3

| | |
|---|---|
| Material to be measured: | H shaped wide flange beam |
| Temperature of material: | 705 ° C (978 °K) |
| | λp = 2.96 μm |
| Radiation energy detector: | Si-Vidicon tube, Wave length of main sensitive spectra being 0.4 μm to 0.73 μm |

In case of detecting a flaw such as scab having a lower temperature under the above conditions;

$$\frac{Wh}{Wl} = \frac{\int_{\lambda_1 = 0.4}^{\lambda_2 = 0.73} Me\lambda d\lambda (T_2 = 978\ °K)}{\int_{\lambda_1 = 0.4}^{\lambda_2 = 0.73} Me\lambda d\lambda (T_1 = 963\ °K)} = 1.322$$

Sn/Wpp = 20 and $$\left(\frac{a}{a-3}\right)^{\frac{1}{\beta}} = \left(\frac{20}{17}\right)^{\frac{1}{0.90}} = 1.184$$

Then it satisfies the formula:

$$\frac{Wh}{Wl} > \left(\frac{a}{a-3}\right)^{\frac{1}{\beta}}.$$

In case of detecting a flaw having a higher temperature such as crack, $$\frac{Wh}{Wl} = \frac{\begin{array}{c}\lambda_2 = 0.73\\ \int_{\lambda_1 = 0.4} Me\lambda d\lambda(T_2 = 983 \overset{\circ}{K})\end{array}}{\begin{array}{c}\lambda_2 = 0.73\\ \int_{\lambda_1 = 0.4} Me\lambda d\lambda(T_1 = 978 \overset{\circ}{K})\end{array}} = 1.322 \text{ and}$$

$$\text{and}\left(\frac{a+3}{a}\right)^{\frac{1}{\beta}} = \left(\frac{23}{20}\right)^{\frac{1}{0.96}} = 1.1567.$$

It thus meets the formula:

$$\frac{Wh}{Wl} > \left(\frac{a+3}{a}\right)^{\frac{1}{\beta}}.$$

On the other hand, in the case of using the same infrared detector element Hg(1 −x) Cd (x) Te as above in which the wave length of the main sensitive spectra is in the range of 2 μm to 5 μm as the radiation energy detector, the formulae:

$$\frac{Wh(T_2 = 978 \overset{\circ}{K})}{Wl(T_1 = 963 \overset{\circ}{K})} = 1.074 \text{ and}$$

$$\text{and}\left(\frac{a}{a-3}\right)^{\frac{1}{\beta}} = 1.081$$

would apply to a flow having a lower temperature such as scab, while the formulae:

$$\frac{Wh(T_2 = 983 \overset{\circ}{K})}{Wl(T_1 = 978 \overset{\circ}{K})} = 1.074 \text{ and}$$

$$\text{and}\left(\frac{a+3}{a}\right)^{\frac{1}{\beta}} = 1.075$$

would apply to a flaw having a higher temperature such as crack.

Thus, the satisfactory S/N can not be obtained since $$\frac{Wh}{Wl} < \left(\frac{3}{a-3}\right)^{\frac{1}{\beta}} \text{ and } \frac{Wh}{Wl} < \left(\frac{a+3}{a}\right)^{\frac{1}{\beta}}.$$

As is obvious from the foregoing description, a detector having a photoelectric conversion element or photo cathode in which the main sensitive spectra is in the range of the wave lengths shorter than the wave length giving the maximum spectral intensity in the radiation energy emitting from a material or hot metal, or a detector having an optical filter capable of transmitting only the radiation energy of this wave length range is optimum for use as a detector for measuring the radiation energy emitting from the material or hot metal. This invention is thus intended to use a television camera as a means to detect the radiation energy in order to detect with high accuracy the difference of the radiation energy caused by the difference of the temperature between the normal part and the defective part of the material or hot metal.

In an ordinary television camera, the video signal is composed of 525 scanning lines and the imaging surface is exposed during the scanning of one frame, usually for 1/30 second. This exposure time of 1/30 second is, however, considerably long for the exposure time of an imaging surface, so that the phenomenon of fading in image by movement may occur in the case where the material to be measured is moving. As a result, a static image of a moving subject of FIG. 7 (b) which should appear if there were no fading in the image gives the rest image of FIG. 7 (a) because of fading in the image. Such an image as shown in FIG. 7 (a) will produce a broken waveform so that a satisfactory value for S/N can not be obtained. In this invention, therefore, a shutter means for shortening the exposure time of the imaging surface of the television camera is provided before the imaging tube in order to obtain a rest image which should be as shown in FIG. 7 (b). Generally, the imaging tube will give some lag. The extent of this lag may vary with the characteristic of each image pick up tube, but it is usually several % to 25%. If this lag occurs as a material to be measured is moving, a signal indicating a flaw may appear at a position where such a flaw can not have existed or where such flaw did exist in the previous frame, which results in higher noise level. On the other hand, if the flaw position of the present frame which was a normal part of the previous frame has a lag, the signal level for the flaw tends to approach to the signal level for the normal part, so that the signal level will be lowered, which will in turn lower the value of S/N.

In view of the above fact, the active shutter timing and the exposure time of the shutter means of the television camera in this invention must be selected in such range where the noise caused by lag can be negligibly small and a fully static image can be otained. In order to accomplish this, the shutter means used in this invention features (a) a rotary disc shutter conducting shutter action synchronizing the blanking period of said television camera, (b) another shutter means having a time of shutter action which is shorter than twice the period of the shutter action of said rotary disc shutter and longer than the time when said rotary disc shutter holds opened and conducting shutter action singly at the synchronizingly triggered time with said rotary disc shutter, and (c) a shutter control circuit.

Also in one aspect, a shutter means may be composed so as to open the shutter of 1/1000 second at the interval of each four frames.

In FIG. 8 is shown one example of a shutter means illustrated by an electric block diagram. A surface image of a material 3 is formed on a photo cathode of an image pick up tube 8 of the television camera through an image-forming lens 7. A rotary disc shutter 9 and an interval shutter 112 are mounted between the image-forming lens 7 and the image pick up tube 8. A vertical synchronization signal produced by a synchronization signal circuit 10 is compared with an output pulse given by a shutter-action-detecting element 12 for detecting an active movement of the shutter 9 by means of a phase-difference detecting circuit 11, whereby an output voltage proportional to the phase difference of the two can be applied to a DC voltage controling circuit 13. This circuit 13 controls the voltage of a DC power source 14 according to the output voltage of the circuit 11 so as to eventually decrease the phase difference between the vertical synchronization signal and the output pulse from the element 12. A shutter action circuit period controlling 15 preliminary sets the output voltage of the DC power source 14 so that the cycle of the shutter action of the shutter 9 becomes about ½ of the cycle of the vertical synchronization signal of the television camera. FIG. 9 is a diagram illustrating the active timing of the high speed shutter means in the example of FIG. 8. FIG. 9, (a) shows the vertical synchronization signal of the television camera (b) shows the active timing of the rotary disc shutter having ½ cycle of the vertical synchronization signal and operating in synchronization with the vertical synchronization signal.

A blanking signal from the circuit 10 and the output pulse from the element 12 are applied to an "AND" circuit 100, which produces an output only when the logical product, "AND" can be obtained, or only when the active timing of the rotary disc shutter exists in the blanking signal. An "AND" circuit 102 produces an output only when the logical product, "AND" can be obtained between a shutter-controlling signal of a shutter-controlling circuit 112 and an output signal of the "AND" circuit 100. Shutter controlling circuit 101 generates a pulse each time a predetermined amount of the material viewed 3 passes the image pick-up tube. Shutter controlling circuit 100 could include the known combination of a pulse generator connected to a measuring roll in contact with material 13 and a present counter which counts the pulses from the pulse generator and produces a pulse when a predetermined number of pulses is counted. Shutter controlling circuit 101 enables the interval shutter 112 to be actuated (in a manner described further below) in synchronism with the rotary disc shutter 9, whose operation is controlled by synchronization signal circuit 10, and the material 3. Such a circuit is disclosed in British Pat. Specification Ser. No. 943,557 filed May 15, 1961. A flip-flop circuit 103 is actuated by each output of "AND", whereby its output terminals Q and $\bar{Q}$ assumes a high or "H" level and low or "L" level alternately. Assuming now that the output terminal Q assumes a "H" level and the output terminal $\bar{Q}$ assumes a "L" level by the output of "AND" circuit 102, a circuit for magnetic excitation 104 generates a +5V pulse of about 50 msec width triggered by the rising signal of the Q output of the circuit 103, while a circuit for reverse directional magnetic excitation 106 generates a −5V pulse of about 2.5 msec width triggered by the rising signal of the Q output of the circuit 103. A circuit for magnetic excitation 105 and a circuit for reverse directional magnetic excitation 107 connected to the output terminal $\bar{Q}$ of the flip-flop circuit 103 do not generate output because the signal change of the output terminal $\bar{Q}$ is decreasing. The output of the circuit 104 is applied to an amplifying circuit 108 and is output therefrom as a pulse of about −15V, 50 msec width after electric power amplification. The output of the circuit 106 is applied to an amplifying circuit 109 and is output therefrom as a pulse of about ±15V, 2.5 msec width after electric power amplification.

If there is an output again from the "AND" circuit 102, the output of the flip-flop circuit 103 is inverted, so that the output terminals Q and $\bar{Q}$ of the circuit 103 become "L" level and "H" level, respectively. Under this condition, the circuits 104 and 106 connected to the output terminal Q do not generate any output pulse, while the circuits 105 and 107 connected to the output terminal $\bar{Q}$ generate a +5V pulse of about 50 msec width and a −5V pulse of about 2.5 msec width, respectively, triggered by the rising signal. The output of the circuit 105 is input applied to the amplifying circuit 109, which eventually generates a pulse of about −15V, 50 msec width. The output pulse of the circuit 107 is input applied to the circuit 108, which eventually generates a pulse of about +15V, 2.5 msec width. In other words, the amplifying circuits 108 and 109 output a pulse of about −15V, 50 msec width and a pulse of about +15V, 2.5 msec width to electromagnets 110 and 111 each time the circuit 103 is inverted. Consequently, an iron piece 113 fixed to an interval shutter plate 112 is pulled to an electromagnet on the side where the circuit 104 or the circuit 105 operates each time the output of the circuit 103 is inverted. After the exciting current is ceased, the pulling condition is retained by the residual magnetism.

When a signal is further input applied to the circuit 103, a pulse current flows in an electromagnet on the pulling side for about 2.5 msec, the direction of said current being opposite to that of the pulling period. Accordingly, the iron piece 113 is instantaneously repelled by the action with the residual magnetism of the piece. Since, at this time an electric current is flowing in the other electromagnet for about 50 msec, which has been excited thereby, the iron piece 113 is strongly pulled to said other electromagnet, and thus the shutter plate 112 can operate each time of the shutter instructions in synchronization with the disc shutter 9. This behavior is shown in (c) and (d) of FIG. 9. As set out above, the interval shutter plate 112 acts with a cycle shorter tha twice the period of the action of the shutter 9 and for a time longer than the time when the shutter 9 holds opened. Therefore, the exposure interval of the image pick up tube 8 is determined by the shutter plate 112, and the exposure time is determined by the time for opening the shutter 9. The behavior of the exposure interval and the exposure time of the image pick up tube 8 is shown (e) of FIG. 9. If the shutter means as shown in the aforesaid example is used, the rotary disc shutter 9 and the interval shutter 112 operate supplementarily with each other, which makes it possible to effect the high speed shutter action at any given timing, whereby the above mentioned problem of fading of the image by movement can be overcome.

In the above example, an electromagnetic type shutter using two electromagnets is shown as the interval shutter, but it can be any other shutter means, such as one utilizing a pulse motor, etc. alternatively, it can be one other than the above described mechanical shutter, which may be an electronical shutter such as the known image-transfer-controlling-type shutter, etc.

As for the correction of output fluctuation in the imaging surface of the image pick up tube of a television camera, there is generally a fluctuation of output voltage called "shading" or "beam landing error" in the image pick up tube of a television camera. This fluctuation of output voltage of the image pick up tube does not give rise to any practical problem in the ordinary television apparatus intended to be used only for visual observation of the video signal of the television camera displayed on a television receiver. However, when it is desired, as in the practice of this invention, to use a television camera as a detector for radiation energy radiated from a material to be measured and thereby to detect a surface flaw of the material by processing the output signal of the television camera in a circuit for recognizing defects, this fluctuation of output voltage of the image pick up tube has a great effect upon the accuracy in detecting the flaw.

Assuming now that a material having such surface flaw such as crack is photographed by an image pick up tube having ordinary output characteristics, the output signal one of its scanning lines shows a wave pattern as shown in FIG. 11 (a). If in this case there are signal wave patterns like 16 and 17 corresponding to the flaws, there may be some troubles that such flaw signals 16 and 17 can not be detected with satisfactory accuracy when these output signal wave patterns are processed by the use of an ordinary circuit for recognizing defects wherein they are triggered by comparison with a predetermined voltage level. In order to avoid such problems, it is necessary that the output of the image pick up tube during times of no received radiation should be constant and that the output fluctuations from the standard surface responding to the change of the intensity of illumination of a material should be minimized. If it is attempted to accomplish this requisite by making the characteristics of the image pick up tube uniform, it becomes necessary to improve or develop the image pick up tube itself, such as controlling the amount of deposit by vacuum evaporation on the photo cathode or unifying the passage of the electron beam on the photo cathode. It is, however, impossible at present to effect such an improvement or development of the image pick up tube itself.

Accordingly, it is pre-requisite in this invention to provide a shading control circuit in order to correct the fluctuations of the output voltage of the image pick up tube of the television camera. This shading control circuit may be positioned between the output terminal of the television camera and the input terminal of the circuit for recognizing defects, and provided with (a) a first envelope detector for detecting the envelope of the output signal wave pattern of one field of a output of the television camera, (b) the first differential amplifier circuit for producing a signal corresponding to the difference between the output signal of the first envelope detector and the output signal of that one field, (c) a first variable amplifier circuit for amplifying the output signal of said first circuit of differential amplifier according to the voltage of the output signal of said first envelope detector, (d) a second envelope detector for detecting the envelope of the output signal wave pattern of one scanning line of the television camera from the output signal of said first variable amplifier circuit, (e) a second amplifier circuit for producing a signal corresponding to the difference between the output signal of said second envelope detector and said output signal of said one scanning line, and (f) a second variable amplifier circit for amplifying the output signal of said second circuit of differential amplifier according to the voltage of the output signal of said second circuit of differential amplifier and responding to the voltage of the output signal of said second envelope detector.

The correction of shading is further described in detail below with reference to FIGS. 10 and 11. FIGS. 10 (a) and (b) shows 262.5 scanning lines of the video signal of the image pick up tube. In this case the abscissa or the axis of time is contracted so that one scanning line shown in FIG. 11 (a) and (b) looks as if it were a single line. FIG. 10 (a) indicates the signal wave pattern before correction of shading is carried out. The envelope of the signal wave pattern of FIG. 10 (a) shows the output fluctuation of the image pick up tube in the vertical direction.

The result of correction of this output fluctuation in the vertical direction is shown in FIG. 10 (b) where the envelope is shown to be horizontal. In FIGS. 11 (a) and (b) is shown the signal wave pattern of one horizontal scanning line taken from FIGS. 10(a) and (b), respectively, and elongated with respect to the axis of time or the abscissa as compared to FIG. 10. FIG. 11 (a) shows the signal wave shape before correction of shading is carried out, from which it is seen that even when the material at same temperature is photographed, the envelope of the signal wave pattern is not horizontal but curved, which indicates the output fluctuation in the horizontal direction of the image pick up tube. The result of correction is shown in FIG. 11 (b). In FIG. 11, the numerals 16, 17, 16′ and, 17′ are the signal wave patterns for flaws, and the 16′, 17′ which are the signal wave pattern of flaws after correction appears above the normal signal level as shown in FIG. 11 (b) because they are taken as the differential signal from the envelope.

FIG. 12 is a block diagram illustrating an example of a control circuit used in this invention which compensates the television camera's shading as well as the temperature difference among normal parts of the observed material. It shows the construction of a wave pattern control circuit 300 for controlling the fluctuation of the standard level and the linear property of the video signal produced by scanning of the television camera 200. Television camera 200 includes image pick-up tube 201, deflection circuit 202, deflection coils 203, preamplitier 204 and amplifier 205. Since these structures are well known in the art, they will not be described in further detail. A part of the video signal produced by scanning which has been amplified by the amplifier 205 of the television camera 200 is applied to the first buffer circuit 301 of the wave pattern control circuit 300, which is then applied to the first envelope detector 302 after its output impedance, voltage level, etc. is regulated. In the first envelope detector 302, a signal representing the envelope of the output signal wave pattern of one field is produced, which signal is then applied to the first differential amplifier circuit 303. A part of the video signal produced by scanning from the amplifier 205 of the television camera 200 is also applied to the circuit 303. In this first differential amplifier circuit 303, the output fluctuation resulting from the shading between fields is corrected, and its output signal is applied to the first variable amplifier circuit 304. The amplification factor of the first variable amplifier circuit 304 is controled by the output voltage of the first envelope detector 302. The output signal of the first variable amplifier circuit 304 is applied to the second buffer circuit 305, which is then applied to the second envelope detector 306 after its output impedance, voltage level, etc. is regulated. In the second envelope detector 306, a signal representing the envelope of the output signal wave pattern within one scanning lie is produced, and this signal representing the envelope is applied to the second differential amplifier circuit 302. On the other hand, a part of the output signal of the first variable amplifier circuit 304 is also applied to the second differential amplifier circuit 307. In this circuit 307, the output fluctuation resulting from the shading within one scanning line is corrected, and its output signal is applied to the second variable amplifier circuit 308. The amplification factor of this circuit 308 is controled by the output voltage of the second envelope detector 306. By carrying out this signal processing, the output signal wave pattern within one field becomes such as shown in FIG. 10 (b) and the output signal wave pattern within one scanning line is such as shown in FIG. 11 (b), whereby the corrected output signal wave pattern include the flaw signal wave patterns 16' and 17' corresponding to the flaw signal wave patterns 16 and 17 of FIG. 11 (a).

In other words, in the wave pattern accompanied by output fluctuations as shown in FIG. 11 (a), it is difficult to detect the flaw signal wave pattern 16 or 17 with good accuracy, while in the flaw signal wave patterns 16', and 17' obtained by the above stated correction of the wave pattern, it becomes possible to detect the flaw signal wave pattern 16' or 17' by the use of an ordinary circuit for recognizing defects with good accuracy.

It is thus possible to overcome the problems resulting from the fluctuation of the output voltage of the image pick up tube in the apparatus for detecting the surface flaw wherein a television camera is used for detecting the radiation energy emitting from a material to be measured, if the ununiformity of the output caused by the shading or beam landing error incidental to the image pick up tube is corrected by the use of such a shading control circit as described hereinabove.

As set out hereinbefore, if a television camera provided with a shutter means for the image pick up tube is used for detecting the radiation energy emitting from a hot material such as hot metal, while a surface flaw detecting apparatus provided with a shading control circuit between the output terminal of said television camera and the input terminal of the circuit for recognizing defects is used, a surface flaw of a hot material or hot metal such as hot steel can be detected with satisfactory accuracy.

In the above description, the mechanism of an apparatus for detecting a surface flaw of a hot material or hot metal by detecting the radiation energy, that is, self-radiant energy, emitting from the material is explained. However, there are some cases, depending upon the particular kind of flaw on the material, that a higher accuracy in detecting the flaw can be obtained if the reflected energy of an illuminating ray from outside is detected rather than if the self-radiant energy of the material is detected. For example, in the case of a crack, a higher value of S/N can be obtained by detecting the reflected energy of a ray originating from outside. However, even this case it is required that the ray originating from outside should be a strobe light. Also the operation of this strobe light and the shutter means should be synchronized with each other, and the radiation condition of this strobe light flash should be optimum for the light reflection characteristic of the flaw of the surface of the material.

The condition for radiating the strobe light in the apparatus of this invention is to provide a pair of strobe means which give substantially symmetrical radiation angles with each other with respect to a line perpendicular to the surface of the material to be measured. In this caae radiation angle $\theta$ should preferably satisfy the following formula.

$$2\alpha max < \theta < 2\delta min$$

wherein:

$\theta$: Radiation angle of strobe light to a line perpendicular to the surface of the material to be measured. (FIG. 17)

$\alpha max$: Maximum inclined angle of projected or recessed parts of the normal part of the material to be measured. (FIG. 16)

$\delta min$: Minimum value among defects to be detected of the maximum inclined angle of projected or recessed parts of a single defective part of the material to be measured. (FIG. 16)

The above described radiation condition for the strobe light is described in detail below with reference to the drawings.

Figure 14:
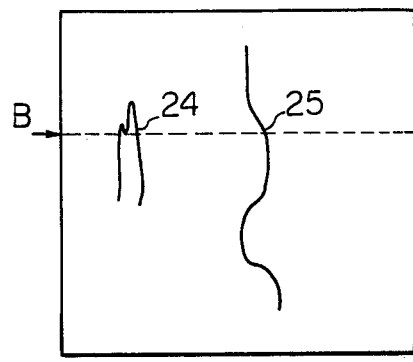
Figure 14:
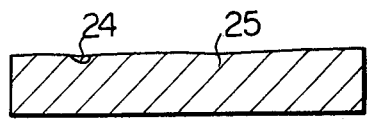
Figure 15:
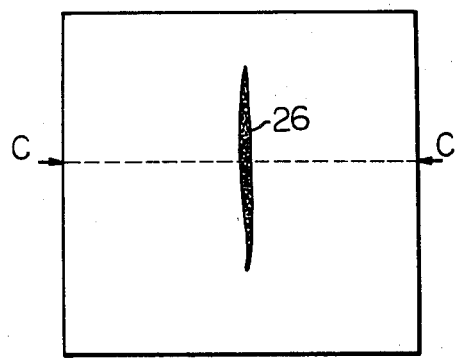
Figure 15:
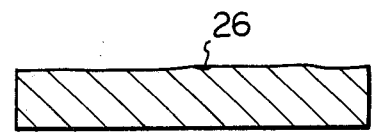

Typical surface flaws of a hot metal are shown in FIGS. 13 to 15. The numerals 21, 22 and 23 of FIG. 13 (a) represent flaws called "needle cracks," which appear as fine cracks as shown in 21, 22 and 23 of FIG. 13 (b) which is a section taken along the line A—A of FIG. 13 (a). The numeral 24 of FIG. 14 (a) represents a scale flaw usually called "scab", and the numeral 25 is a flaw called a crack, the sectional views (B—B in FIG. 14 (a) of which are shown as 24 and 25 in FIG. 14 (b), respectively.

The above flaws represented by the numerals 21 to 25 appear as relatively fine lines with respect to the part exposed on the surface, the depth of which is longer than the width of the opening. The flaw shown as the numeral 26 in FIG. 15 (a) is caused by being rolled while entangling some refractory materials or scales, which results in a shallow light-absorbing material embedded therein as shown in FIG. 15 (b) (C—C section of FIG. 15 (a)).

On the other hand, the surface of a normal part of the material to be measured is not perfectly flat or smooth, but somewhat rugged. This ruggedness will disturb the direction of reflection of the illuminating rays, change the amount of radiation to the light-receiving system (television camera), and produce the same signal as the flaw signal, which gives rise to a noise component. It is explained by way of FIG. 16 which is an enlarged sectional view illustrating an irregularity in the normal part and the irregularity in the defective part of a material 27 to be measured. The irregularity 28 of the normal part is relatively shallow as compared with the width of the opening, and the angle $\alpha max$ made by the average normal surface 29 and the maximum inclined surface is relatively small. In contrast thereto, the angle $\delta$ made by the average normal surface 29 and the maximum inclined surface for the defective part 30 having a crack is as large as about 90°. The radiation angle $\theta$ of the strobe light is defined as the angle made by the line N perpendicular to the average normal surface of the material 27 and the center line M of the radiated ray from the radiation source 901 when the center line M of the radiated ray is directed to the center point S of the visual field over the material 27 of the light-receiving system (television camera) 200.

The values of $\alpha max$ and $\delta min$ are shown below as a result of practical experiment.

By way of an example of a surface condition which can be considered as the normal part but has a relatively large ruggedness, FIG. 19 shows such a surface condition of a steel material which has been subjected to overall hot scarfing. As shown in FIG. 19, there are banded stripes 32 and 33 on the surface of the steel material 31. Enlarged views thereof are shown in FIGS. 19 (b) and (c), respectively. The $\alpha max$ of the banded stripes is about 10°. The $\delta min$ of the defective parts as exemplified by the flaws 21 to 25 shown in FIGS. 13 and 14 is usually 80° to 90°. The brick flaw or the bitten scale flow, etc. shown in FIG. 15 are flaws of a light-absorptive nature, and the defective part will give a smaller amount of reflected light for any angle of illumination and show a clear flaw signal so that the angle of the inclined surface will not cause any problem.

The result of actual measurement of the behavior of the light reflection is shown in FIG. 18. In this figure, the illumination angle of the strobe light shown in FIG. 17 is indicated by the angle shown on the circumference of a semi-circle, and the strength of the reflection light in this direction is indicated as the strength relative to the condition of $\theta = 0°$.

The measurement of $\theta = 0°$ is made by the use of a half mirror.

The strength of the reflected light obtained in the case of an illuminating strobe light in one direction only as shown in FIG. 17 is equivalent to that obtained in the case of an illuminating flash at an angle in the range of $\theta \pm 2\alpha$ and receiving the light in the vertical direction, because the normal part is not perfectly smooth as described before and thus the direction of the reflected light fluctuates. Accordingly, the fluctuation in the photoelectric conversion of the light-receiving system (television camera) becomes very large even in the normal part, which will act as the noise fluctuation component.

Since the signal for a flaw is substantially constant about the same flaw under the above conditions, the value of S/N becomes small unless the noise fluctuation component is made as small as possible.

In case of illumination at an angle of $\theta$ in one direction as shown in FIG. 17, the strength of the reflected light signal $\phi(\theta)$ fluctuates in the range from $\phi(\theta + 2\alpha)$ to $\phi(\theta - 2\alpha)$ if the inclination of the ruggedness of the normal surface is in the range of $\pm \alpha$. This relation corresponds to a considerable fluctuation in view of FIG. 18 showing the reflection behavior.

Now as taught by this invention, if the strobe light is radiated in two directions which are mutually symmetric with respect to the line perpendicular to the surface of the material to be measured, that is, in both the illumination angles of $\theta$ and $-\theta$, the strength of the reflected light of the normal part becomes $\phi(\theta + 2\alpha) + \phi(\theta - 2\alpha)$ because of the symmetry of the reflection behavior. In the range of small values of $\alpha$, it may be substantially offset and hence the following formula can always be given:

$$\phi(\theta + 2\alpha) + \phi(\theta - 2\alpha) \simeq 2\phi(\theta)$$

As for the reflected light coming from the defective part, the angle $\delta$ made by the maximum inclined surface of the defective part is nearly 90°. Therefore, even in case that the strobe illumination is carried out in two directions, the strength of reflected light in the direction of the light-receiving system is substantially the same as that in case of illumination in one direction, so that the difference between the two is negligible. Accordingly, the amount of the reflected light coming from the defective part does not change and the fluctuation of the normal part or noise becomes small, which results in a remarkable enhancement of the S/N value.

In case the ruggedness of the normal part is very fine and distributed substantially uniformly on the surface of the material to be measured and that each individual protrusion or recess of that ruggedness is small as compared with the size of the resolving power of the flaw detecting system, the surface of the material can be considered as smooth and it will thus cause no trouble in practical use to radiate the strobe light in one direction only. In passing, the ruggedness of the normal part in which it is recognized as particularly desirable for the illumination to be applied in two directions is such that the width of the ruggedness is about 0.3 mm or more and the length thereof is about 1 mm or more.

The reason why the illumination angle $\theta$ of the strobe light should preferably be $2\alpha\max < \theta < 2\delta\min$ is described below.

The fundamental reason is that it is necessary to establish the relation between the illumination and the light receiving system so as not to include the regular reflection condition, because the direction of regular reflection yields a condition that the amount of light reflected becomes particularly large. Because it gives the maximum curvature and the maximum strength of reflected light as shown in FIG. 18 the formula:

$$\phi(\theta + \Delta\alpha) + \phi(\theta - \Delta\alpha) \simeq 2\phi(\theta)$$

can not be satisfied. The optimum relation should thus be $2\alpha\max < \theta < 2\delta\min$.

The practial limitation is of course to utilize the range where the curvature of the curve shown in FIG. 18 is not very large, and hence the condition of $2\alpha\max \simeq \theta$ is not desirable. Moreover, the measurement can not be carried out if $\theta \geq 90°$. Therefore, it is best practiced under the condition:

$$2\alpha\max < \theta < 90°.$$

if the $\delta\min$ is about 80° as mentioned above.

In FIG. 17 is shown an example in which a light-receiving system (television camera) 200 is set for vertical overlooking and arranged such that a line connecting the center of the ray axis of the system 200 and the perpendicular center point S of the visual field is aligned with line N perpendicular to the surface of the material 27. In the practice of this invention, however, the overlooking angle of the light receiving system does not always have to be vertical so long as the noise level is made relatively small while the S/N made large so that the accuracy of detection can be practically increased. For example, in FIG. 17, it is practically feasible that the overlooking angle of the light-receiving system 200 be angled a certain degree, for example, by about 20°, to the line N within the plane which intersects the paper surface at right angles and includes the perpendicular line N.

Similarly, it is also feasible that the direction of radiation of the light source 901 is angled by the certain degree within a plane which intersects the paper surface at right angles and includes the middle line M of the illumination light of FIG. 17.

An example for detecting a surface flaw on a hot steel after blooming by the use of the apparatus of this invention is described hereinbelow.

FIG. 20 is intended to explain a method for detecting a surface flaw of a hot steel material which has been subjected to blooming.

From nozzles 42, 42' for descaling mounted after a blooming mill 41, a water jet having at least 60 Kg/cm² of the nozzle end pressure is blown to the upper and lower surfaces of the steel material during the return pass before the finish pass or immediately after the finish pass, whereby the scale on the surface of the material which gives rise to an obstacle signal is removed to the flaw signal. The steel material 43 as rolled is conveyed toward television cameras 45, 45′ by a roller table 44. Just before the television cameras 45, 45′, water shower nozzles or air nozzles 46, 46′ having the nozzle end pressure of about 20 Kg/cm$^2$ are provided so as to blow off the scale and water drops remaining on the surface of the material which give rise to said obstacle signal as well as to cool the surface layer of the steel material. The surface layer of the steel material thus cooled is immediately allowed to recover its temperature by virtue of transmission of heat from inside the material. Owing to the difference of time for heat recovery between the normal parts having no flaws and the defective parts having some flaws, the difference of the temperature of the surface of the material between the normal parts and the defective parts is increased. The difference of the radiation energy caused by that difference of the temperature of the surface of the material is then detected by the television cameras 45, 45′.

The television cameras 45, 45′ are provided with the above described shutter means (not shown), and therefore the severe radiation energy radiation from the steel material at high temperature can be restricted to a suitable amount and also a rest image of the surface to be measured can be obtained.

In FIG. 20, the apparatus subsequent to the television cameras 45, 45′ are omitted. However, it is to be noted that the circuit for shading correction is connected to the output terminal of the television camera, and the output of the television camera is applied to the circuit for recognizing defects after the output fluctuations of the image pick up tube of the television camera is corrected. In the circuit for recognizing defects, the flaw signal is taken out at a predetermined slice level. The subsequent signal processing is carried out such as, for example, that this flaw signal is converted into a digital signal, applied to an "AND" circuit with a clock pulses, the number of the flaw signal pulses which are included in the total length of the scanning line of a field constituting one frame of the television camera is counted, and the defect area ratio in the field is calculated using this count. The flaw information of the hot steel material after blooming thus obtained is utilized for controling the depth of scarfing in the subsequent step of hot scarfing which is carried out for removing flaws from the hot steel material. Furthermore, it is also possible to conduct a partial scarfing of the material in the hot scarfing step by determining the position where the flaws have appeared and using this information for the position of the partial scarfing.

In this way, the apparatus of this invention makes it possible to detect a flaw of the surface of the steel material after blooming and thereby to carry out the proper control of the depth or area of scarfing in the hot scarfing step. Therefore, a loss of yield which has heretofore been caused by scarfing of a part where there is no flaw can effectively be avoided. Moreover, there is no need for conventional step of once cooling the material, detecting the flaws thereof and removing the flaws under cooled conditions, which results in an advantage that a hot steel material at high temperature can be passed, without cooling, to the next step or to the reheating furnace in a rolling plant so that heat energy can be fully and efficiently utilized.

We claim:
1. An apparatus for detecting a surface flaw in a moving material to be measured wherein the radiation energy from the surface of said material at high temperature is detected by means of photoelectric detector so as to detect the surface flaw of said material, which comprises:
   (1) a television camera having an image pick-up tube for detecting the radiation energy from the surface of said material;
   (2) a shutter means provided before said image pick up tube of said television camera to obtain the rest image of the moving material by said television camera;
   (3) a shading control circuit receiving the output of said television camera for correcting the output fluctuations within an image pick up plane of said image pick up tube of said television camera; and
   (4) a defect recognizing means receiving the output of said shading control circuit for recognizing defects in the material.

2. The apparatus according to claim 1 in which said shutter means comprises: (a) rotary disc shutter for conducting shutter action synchronously with the blanking period of said television camera; (b) a further shutter means having a time of shutter action which is shorter that twice the period of the shutter action of said rotary disc shutter and longer than the time when said rotary disc shutter holds opened; (c) a shutter control circuit for conducting the shutter action of said further shutter means synchronizingly with said rotary disc shutter.

3. The apparatus according to claim 1 in which said shading control circuit comprises: (a) a first envelope detector for detecting the envelope of the output signal wave pattern of one field of the output of said television camera; (b) a first differential amplifier for producing a signal corresponding to the difference between the output signal of said first envelope detector and the output signal of said one filed; (c) a first variable amplifier for amplifying the output signal of said first differential amplifier according to the voltage of the output signal of said first envelope detector; (d) a second envelope detector for detecting the envelope of the output signal wave pattern of one scanning line of said television camera from the output signal of said first variable amplifier; (e) a second differential amplifier for producing a signal corresponding to the difference between the output signal of said second detector and the output signal of said one scanning line; and (f) a second variable amplifier for amplifying the output signal of said second differential amplifier according to the voltage of the output signal of said second envelope detector.

4. The apparatus according to claim 1 further comprising a pair of strobe means for illuminating the surface of the material an angles substantially symmetrical with each other with respect to the normal line to the surface of said material synchronously with the shutter action of said shutter means.

5. The apparatus according to claim 3 further comprising a pair of strobe means for illuminating the surface of the material at angles substantially symmetrical with each other with respect to the normal line to the surface of said material synchronously with the shutter action of said shutter means.

* * * * *